(12) United States Patent
Bechtel et al.

(10) Patent No.: US 10,194,805 B2
(45) Date of Patent: Feb. 5, 2019

(54) INTRINSIC AND SWEPT-SOURCE RAMAN SPECTROSCOPY

(75) Inventors: Kate Leeann Bechtel, Pleasant Hill, CA (US); Brian Patrick Wilfley, Los Altos, CA (US)

(73) Assignee: Triple Ring Technologies, Inc., Newark, CA (US)

(*) Notice: Subject to any disclaimer, the term of this patent is extended or adjusted under 35 U.S.C. 154(b) by 239 days.

(21) Appl. No.: 13/367,309

(22) Filed: Feb. 6, 2012

(65) Prior Publication Data

US 2012/0203114 A1   Aug. 9, 2012

Related U.S. Application Data

(60) Provisional application No. 61/439,840, filed on Feb. 5, 2011.

(51) Int. Cl.
*A61B 5/05* (2006.01)
*A61B 5/00* (2006.01)

(52) U.S. Cl.
CPC .......... *A61B 5/0075* (2013.01); *A61B 5/7239* (2013.01)

(58) Field of Classification Search
CPC ............................ A61B 5/0075; A61B 5/7239
USPC ....................................................... 600/476
See application file for complete search history.

(56) References Cited

U.S. PATENT DOCUMENTS

| 4,843,351 | A | * | 6/1989 | Edwards et al. | 332/103 |
| 5,071,416 | A | * | 12/1991 | Heller et al. | 606/3 |
| 5,373,358 | A | * | 12/1994 | Adachi | 356/301 |
| 6,321,111 | B1 | * | 11/2001 | Perelman et al. | 600/477 |
| 6,345,194 | B1 | * | 2/2002 | Nelson et al. | 600/425 |
| 2007/0049809 | A1 | * | 3/2007 | Bechtel et al. | 600/316 |
| 2008/0117416 | A1 | * | 5/2008 | Hunter et al. | 356/301 |
| 2008/0312879 | A1 | * | 12/2008 | Fortier et al. | 702/189 |
| 2010/0302535 | A1 | * | 12/2010 | Lipson et al. | 356/301 |

OTHER PUBLICATIONS

Kienle, A., et al. ("Spatially resolved absolute diffuse reflectance measurements for noninvasive determination of the optical scattering and absorption coefficients of biological tissue." Applied Optics 35(13): 2304-2314; 1996.*

* cited by examiner

*Primary Examiner* — Jonathan Cwern
(74) *Attorney, Agent, or Firm* — Sabrina N. David; Joseph T. Lin

(57) ABSTRACT

The present invention pertains to a method and an apparatus for Raman spectroscopy of human tissue. Human tissue is illuminated with a laser emitting a first wavelength of light. A Raman signal is measured and optical properties are determined at this wavelength such that the measured Raman signal can be corrected based on determined optical properties. Determined optical properties may be the scattering coefficient and absorption coefficient of the tissue. A system for Raman spectroscopy of human tissue includes a frequency sweeping laser light source for illumination, and a filtered detector for collecting the Raman signal.

15 Claims, 8 Drawing Sheets

INTRINSIC AND SWEPT-SOURCE RAMAN SPECTROSCOPY

RELATED U.S. APPLICATION

This application claims priority to the U.S. provisional patent application, Ser. No. 61/439,840, entitled "Swept-Source Raman Spectroscopy," with filing date Feb. 5, 2011, which is hereby incorporated by reference in its entirety.

FIELD OF THE INVENTION

The present invention pertains to the field of Raman spectroscopy. The present invention pertains more particularly to Raman spectroscopy performed on human tissue.

BACKGROUND

The original implementation of Raman spectroscopy utilized a scanning monochromator; the Raman scattered light was passed through a slit, the width of which contributes to the frequency resolution, onto a diffraction grating, which bent the remaining light to various degrees corresponding to wavelength. The exit slit of the monochromator selected a narrow band of wavelengths to be measured by the single element detector. The grating was then rotated or the slit translated in order to trace out the Raman spectrum on the detector as a function of time.

Another implementation is Fourier-Transform (FT) Raman spectroscopy, in which Raman scattered light is collimated and passed into an interferometer and then onto a single element detector. Frequency resolution can be obtained by mechanically translating one mirror of the interferometer, which results in an interferogram traced out on the detector as a function of time. The interferogram can be Fourier transformed to obtain the Raman spectrum. Advantages of FT-Raman systems include the multiplex, or Fellgett, advantage and optical throughput, or Jacquinot, advantage. The multiplex advantage is obtained because all or nearly all of the Raman scattered light from the sample is captured by the detector. This can be compared to the scanning monochromator case, in which only one wavelength or narrow band of wavelengths is measured at a time. The optical throughput advantage is obtained because no slits or gratings are required for operation, which would otherwise limit the number of photons reaching the detector.

The other advantage of FT-Raman systems is that they can utilize a 1064 nm laser for excitation, which can greatly reduce the amount of fluorescence background measured from many samples. However, FT systems are bulky, costly, and typically not portable due to mechanical stability requirements. FT systems are rarely, if ever, used for in vivo clinical applications.

The advent of the charge-coupled-device (CCD) detector allowed for "dispersive" Raman spectroscopy. Dispersive Raman systems have the same front end as systems utilizing a scanning monochromator; Raman scattered light is collected and passed through a slit, the width of which can determine the frequency resolution, and then onto a diffraction grating. However, rather than use an exit slit and a single element detector to trace out the Raman spectrum as a function of time, dispersive systems utilize 1-D or 2-D detector arrays or CCDs to image the entire Raman spectrum at once. Dispersive systems have a multichannel advantage in that all of the wavelengths are measured in parallel, or simultaneously, as opposed to the serial, or sequential, measurements of the other implementations. However, dispersive systems have limited optical throughput due to the use of an entrance slit and grating.

SUMMARY

The present invention pertains to a method and apparatus for Raman spectroscopy of human tissue. A method for Raman spectroscopy of human tissue involves illuminating human tissue with a laser emitting light at a first wavelength, determining optical properties of human tissue at the first wavelength, measuring Raman signal from human tissue at a first Raman wavelength, and correcting the Raman signal based on optical properties at the first wavelength. The method can further comprise determining diffuse reflectance of human tissue at the first wavelength, determining scattering coefficient of human tissue at the first wavelength and determining absorption coefficient of human tissue at the first wavelength, deriving a temporal point spread function of an optical signal of human tissue at the first wavelength, or sweeping the laser over a range of wavelengths. The method can further comprise determining scattering coefficient of human tissue at the first wavelength based on the temporal point spread function and determining absorption coefficient of human tissue at the first wavelength based on the temporal point spread function. The first Raman wavelength can be a Stokes Raman wavelength or Anti-Stokes Raman wavelength.

In another embodiment, a method for Raman spectroscopy of human tissue involves illuminating human tissue with a laser emitting light at a first wavelength, determining scattering coefficient of human tissue based on light from human tissue, determining absorption coefficient of human tissue based on light from human tissue, measuring Raman signal from human tissue at a first Raman wavelength, and correcting the Raman signal based on the scattering coefficient and the absorption coefficient. The first Raman wavelength can be a Stokes Raman wavelength or Anti-Stokes Raman wavelength. The method can further comprise deriving time domain characteristics of light from human tissue, deriving time of arrival of photons of light from human tissue, or sweeping the laser over a range of wavelengths. The scattering coefficient of human tissue can be determined at the first wavelength and absorption coefficient of human tissue can be determined at the first wavelength.

In another embodiment, a system for Raman spectroscopy of human tissue comprises a frequency sweeping laser light source for illuminating human tissue, a filter positioned in an optical path after the laser light source and human tissue for allowing Raman wavelengths of light from human tissue to pass through the filter, and a detector positioned behind the filter for detecting an optical signal of the Raman wavelengths of light from human tissue. The system can further comprise an optical analyzer optically coupled to human tissue for determining scattering coefficient and absorption coefficient of human tissue. The filter can be tilted at an angle off-axis with respect to light from human tissue. The system can further comprise a signal generator to generate a digital modulation signal associated with a pseudo-random code sequence and a processor to derive a temporal point spread function of human tissue from light from human tissue or a second detector to detect an optical signal of light reflected from the filter.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Figure 1:
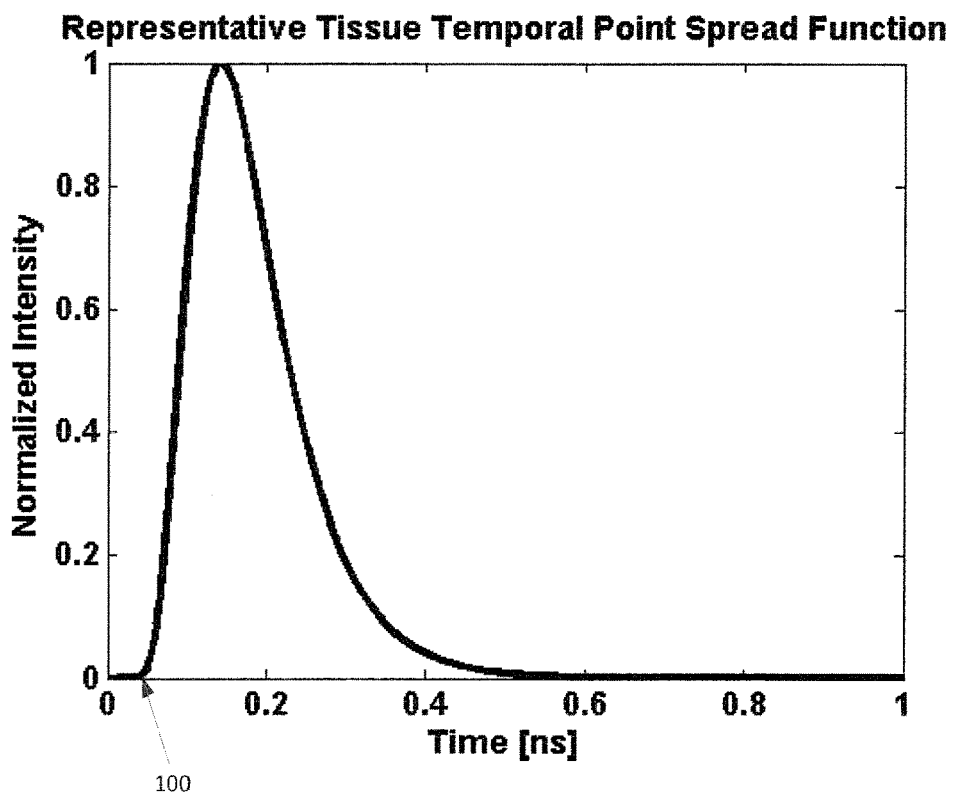
FIG. 1 is a diagram illustrating a representative tissue temporal point spread function of one embodiment of the present invention.

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

All molecules have a characteristic set of vibrational and rotational frequencies that depend on the atoms and atomic bonds they comprise. Raman spectroscopy is very useful because it allows certain vibrational and rotational frequencies of a molecule to be probed optically with any wavelength. It may therefore be used on samples of unknown composition, potentially to gain information regarding their composition.

For a vibration to be visible in a Raman spectrum, i.e. detectable using Raman spectroscopy, the vibration must change the polarizability of the molecule. (Polarizability refers to the ease of which a molecular structure can be altered in a way that unequally distributes the electron cloud.) As a point of comparison, for a vibration to be visible in an infrared absorption spectrum, the vibration must change the dipole moment of the molecule, the dipole moment being an electromagnetic property of molecules.

The energy associated with an electromagnetic, e.g. light, wave is inversely proportional to its wavelength. Raman scattering is an inelastic scattering process in which light is scattered by a molecule and either takes energy away from the vibrating molecule, thereby shortening the wavelength of Raman scattered (Anti-Stokes Raman), or loses energy to the molecule, increasing the vibration of the molecule and emerging with longer wavelength (Stokes Raman). Both Anti-Stokes and Stokes Raman scattering events are quite rare; Stokes Raman scattering occurs in only one out of every $10^7$ photons interacting with a sample, and Anti-Stokes Raman is about 100 times less likely to occur than Stokes Raman. Stokes Raman is therefore more commonly measured. The probability of Raman scattering depends on excitation wavelength ($\lambda$), decreasing by a factor of $\lambda^4$.

To acquire a Stokes Raman (hereby referred to simply as Raman) spectrum, excitation light of a known frequency can be shined onto a sample, and light that has been shifted to longer wavelengths measured. Analysis of frequency differences between the Raman-scattered light and the excitation light can yield the characteristic vibrational and rotational frequencies of the sample. Note that spectroscopic frequencies may be reported in wavenumbers, defined as $1/\lambda$ where $\lambda$ is the wavelength of light in cm. For example, if 785 nm light is shined onto the sample, the Raman scattered light that corresponds to a frequency shift of 500 to 1800 cm$^{-1}$ is collected from 817 to 914 nm. Wavenumbers can be linearly related to energies whereas wavelengths may not be linearly related to energy. The region of frequencies from 500 to 1800 cm$^{-1}$ may be called the "fingerprint" region because it may be used to identify unique organic molecules. The entire frequency shift region from 1 to 4000 cm$^{-1}$ may be collected and provide information about the molecules composing the sample of interest. For medical applications, the Raman spectral range of interest can be within the range of 500 to 1800 cm$^{-1}$. This frequency includes the fingerprint region as well as a region of frequency shifts that may be used to identify the presence organic double bond stretches. Measurements may also extend the region to include frequency changes associated with the C—H and O—H stretches at 2750 to 3400 cm$^{-1}$. Identification of organic double bonds, C—H and O—H bonds can aid in the determination of molecules present in a sample. Embodiments of the present invention may collect Raman signals at wavelengths or frequencies corresponding to shifts between 1 and 4000 cm$^{-1}$, between 200 and 2000 cm$^{-1}$, between 500 and 1800 cm$^{-1}$, between 2750 and 3400 cm$^{-1}$, or any combination or subset thereof.

Determination of the ideal excitation wavelength for performing Raman spectroscopy on many samples, including tissue, may involve a number of competing factors. In order to achieve good penetration depth, a wavelength may be chosen where the absorption and scattering coefficients of the sample are minimized; the degree to which light is scattered or absorbed in a medium can depend on the wavelength of incident light. The "diagnostic window" for which the absorption and scattering coefficients are minimized for many biological samples, including tissue occurs between 700 and 1550 nm.

Because Raman scattering can be quite rare, the presence of fluorescence can often overwhelm the Raman signal; large fluorescence background in a spectrum can make it difficult, if not impossible, to resolve the relatively small peaks attributable to Raman scattering. Therefore, it can also be desirable to reduce the fluorescence background in order to better measure Raman scattering. Fluorescence may be reduced by using relatively long excitation wavelengths; while it may be difficult to entirely avoid excitation and resultant fluorescence from all or most atoms in a sample, longer (i.e. lower energy) wavelengths can lower the probability that excitations will occur. However, there are tradeoffs associated with using longer excitations wavelengths; the amount of Raman scattering that may occur is reduced by a factor of $\lambda^4$ of the incident wavelength, and detectors may be less sensitive to low energy, e.g. long wavelength, light.

An additional advantage to longer wavelength excitation may be improved penetration depth in many samples, including biological tissue. Optical coherence tomography (OCT) systems, for example, utilize 1300 nm light for optimal penetration. While tissue scattering is greatly reduced at longer wavelengths, absorption, primarily from water, is increased. The region for optimal penetration depth can be between 1050 and 1550 nm, depending on the application.

Upon laser excitation of a turbid sample, such as a pharmaceutical pill or tablet or biological media, such as blood, tissue, saliva, or urine, excitation light can be scattered and/or absorbed to varying degrees prior to Raman scatter, and Raman-scattered light can be subject to subsequent scattering and/or absorption as it propagates through the sample. The scattering and absorption properties of a medium can alter the acquired Raman signal from that which would be obtained in a clear medium with no absorption or scattering. Specifically, the amount of signal detected may be increased in a medium where Raman-scattered light undergoes multiple scatterings that increase the optical path length or increase scatter towards the detected region. Alternatively, the signal may be decreased in a medium where Raman-scattered light is scattered away from detected region or absorbed. Further, the shape of the signal may be affected as a result of the wavelength-dependent nature of the applicable absorption and/or scattering coefficients.

The ability to obtain quantitative Raman measurements, e.g. measurements without the effects of sample absorption or scattering, is paramount in many applications involving turbid media. For example, in pharmaceutical analysis of tablets, caplets, or liquid suspensions, the highly scattering and often absorbing coatings or additives can disguise the Raman signal of the active pharmaceutical ingredient (API). In biomedical applications, the determination of analytes such as glucose in blood or tissue may be greatly improved by removing the obscuring effects of absorption and scattering from the Raman signal. In cancer diagnosis, Raman can be an effective modality for discriminating between benign and malignant tissue in vivo for a variety of tissues including breast, oral, and cervical, fitting to a morphological model being one method for doing so. However, the relative contribution to the spectrum of tissue constituents such as collagen, fat, and beta carotene may vary according to the optical properties of the tissue and whether a layer of blood is present on the surface. Correcting for these variations may improve the accuracy of the fit coefficients and therefore the success of the algorithm.

Dispersive Raman systems can be used for clinical applications, including in vivo applications. While these systems can be made portable and handheld, true miniaturization is not immediately feasible. "True" miniaturization may refer to the creation of a chip-sized device or similarly small device. Miniaturization may be desirable as Raman spectroscopy may then be incorporated in multi-functional handheld analytic devices, or may be found desirable in other applications.

Silicon, the material basis for most CCD detectors, can drop sharply in detection efficiency between 1000 to 1100 nm. Therefore, given the benefits of staying within the diagnostic window (700 to 1500 nm), using as long an excitation wavelength as possible for good penetration, and remaining within the region of operation for a silicon CCD camera, dispersive Raman spectroscopy can be performed at either 785 nm or 830 nm. The recent advent of InGaAs array detectors allows for use of 1064 nm excitation with dispersive Raman systems. However, InGaAs can exhibit much higher noise and less sensitivity than silicon. Germanium is another detector material and is more sensitive than InGaAs when cooled to liquid nitrogen temperatures. A relatively new material called "black silicon" exhibits higher sensitivity than either silicon or InGaAs and can detect wavelength as long as 1200 to 1300 nm but can be difficult to obtain.

Turbid can be a descriptor for samples, biological or other, in which molecules can scatter or absorb incident light. Furthermore, in turbid media the absorption and scattering coefficients $\mu_a$ and $\mu_s$ may vary throughout the sample volume. Analogously, water and other liquids are referred to as turbid if they are cloudy or hazy in appearance. Quantitative or intrinsic measurements can refer to true or absolute values, e.g. values that would be obtained regardless of the turbidity of a sample or if all turbidity were removed.

Time-domain methods may be compared or contrasted with frequency-domain methods; hardware used for spectroscopic methods may affect the decision whether to collect optical data in the so-called time domain, e.g. signals reported corresponding to their time of detection, or frequency domain, e.g. reporting changes in signal amplitude or phase. Signals in the time domain and frequency domain may be mathematically related by a Fourier transform. A point spread function (PSF) can be used as a measure of system performance or image quality; the function can map how sharply a system responds to a sharp point—whether the response is concentrated at the point or spread around it or otherwise moved relative to it. A temporal point spread function (TPSF) can map this sort of system response to an impulse in time. FIG. 1 is a diagram illustrating a representative temporal point spread function for tissue. Impulses, such as a photon being released by a source, may be assumed to occur at time t=0 ns along the x-axis. The representative tissue temporal point spread function of FIG. 1 may then represent the response of, or signal reported by, a photodetector in response to said impulses. For example, if a series of photons or impulses were released by a source, then the y-axis of FIG. 1, "Normalized Intensity" may represent the relative number of photons that reached a photodetector "x" number of nanoseconds after being released. In the representative example of FIG. 1, it can be seen that most photons traveled through tissue for approximately 0.15 ns between release and detection.

In one embodiment of the present invention, quantitative Raman measurements may be obtained from turbid media by utilizing a time-domain method to determine optical properties at the excitation wavelength. A time-domain Near-Infrared Spectroscopy (NIRS) signal can be obtained with the aid of a picosecond laser and a single photon counting detector. If the time of arrival of each photon is recorded and a histogram is built up over time, an envelope drawn around the photon arrival histogram can represent the temporal point spread function (TPSF) of the sample. In FIG. 1, then, time t=0 ns may represent the emission of a photon into the tissue. As this representative tissue temporal point spread function may have been created by multiple emission events, it may represent the relative probabilities of an emitted photon reaching a detector located at a fixed distance from the source at various times after emission.

A constructed TPSF can be fit with diffusion theory, e.g. with a variety of boundary conditions in order to uniquely extract the absorption and scattering coefficients, $\mu_a$ and $\mu_s$ respectively. Alternatively, a constructed TPSF can be fit with multi-layer diffusion theory or compared to Monte Carlo-simulated TPSF's of known input parameters. Both of these methods can account for complexities beyond a single homogeneous layer. However, the equipment costs associated with common implementations of TPSF construction can be high and the integration times necessary to build up adequate signal-to-noise histograms for accurate fitting long.

One embodiment of the present invention includes code modulation of a diode laser, either directly or indirectly through use of an external modulator, using any selection of a pseudo-random sequence. The modulation may be any pseudo-random sequence including Golay, Galois, Gold, Kasami, Pseudo-Random Binary Sequence (PRBS), or any other codes that possess the properties of large auto-correlation properties and low cross-correlation values. Cross-correlation is essentially a measure of the similarity of two signals or functions, where a time offset will not be counted as dissimilarity. Auto-correlation refers to the cross-correlation of a function or signal with itself.

The resulting optical signal from the sample may be collected with a fast photodetector. The cross-correlation between the received optical signal with the pseudo-random sequence of the excitation source can be used to relate detected photons to their respective times of origin. Code sequences may be utilized with high auto-correlation values and low cross-correlation values such that cross-correlation between an excitation modulation signal and a detected optical signal can be used to associate features in a detected optical signal with the excitation source impulses which generated them. More details on code selection and demodulation methods are provided in the section, "Exemplary code modulation." Use of pseudo-random sequence(s) can enable the collection of sufficient data to generate a TPSF for a sample in a single measurement, significantly decreasing the time necessary for said generation compared to conventional time-domain methods.

A Raman excitation laser can utilize code modulation using a pseudo-random sequence. The modulation may be any pseudo-random sequence including but not limited to Golay, Galois, Gold, Kasami, or PRBS. The light may be modulated at any depth from 0% to 100% of its maximum intensity. It may be advantageous to modulate the excitation light at less than full amplitude so that the overall power for generating Raman signal is greater than 50% of the maximum available intensity. In qualitative terms, it may not be desirable to allow the excitation light to drop below some threshold intensity very often, as low-intensity excitation light may not create a Raman signal as large (and hence, distinguishable) as the Raman signal from high-intensity excitation light.

A dc component of the excitation light, if it exists, may be subtracted from the received signal prior to cross-correlation with the modulating sequence. Alternatively, a dc component may be effectively removed during cross-correlation by utilizing a bipolar representation of the source modulation code, e.g. a code comprised of −1's and 1's, rather than a unipolar representation of the source modulation code, e.g. a code comprised of 0's and 1's. A detected signal may be inherently "unipolar"; light may be detected (1) or not detected (0), but not "anti-detected" (−1). Therefore, if a detected signal is cross-correlated with another unipolar code, cross-correlation values may peak in appropriate locations but drop in amplitude by only about half where no correlation should be indicated. However, if the unipolar detected signal is cross-correlated with a bipolar code modulation signal comprising −1's and 1's, correlation peaks remain and correlation values elsewhere go to zero. The source modulation code may be represented as −1's and 1's for the purposes of cross-correlation as these calculations are carried out in a processor and may not be directly couple to physical inputs or outputs, such as light being "on" or "off."

Light can be delivered to and collected from a sample in a variety of geometries, including but not limited to: through a hole in a collection optic such as a lens or off-axis paraboloidal mirror, with or without a mask; by displacement of delivery and collection optics for spatially offset Raman (SORS); through any number and arrangement of delivery and collection optical fibers set any given distance apart; delivery and collection at 90 degrees, 180 degrees, or any angle from 0 to 180 degrees with respect to one another; or in transmission mode, e.g. with an optical source and detector located on opposite sides of sample. It is likely the exact algorithm for correction for spectra obtained using a given system will have some dependence on the geometry of the selected delivery and collection optics.

In one embodiment of the present invention, resulting Raman spectra may be time-integrated to obtain a good signal-to-noise ratio (SNR); summing the Raman signal from multiple excitation events within a given time window may increase the height and visibility of the Raman peaks relative to background noise. A result of time-integration may be that rapid amplitude modulation of the excitation source and resultant Raman spectra may not be visible. However, the excitation source may be amplitude modulated in order to obtain the TPSF of excitation-wavelength light, and the effect on acquisition of the Raman signal may be an increased length of integration time necessary to obtain a given SNR relative to the integration time necessary without amplitude modulation of the excitation laser. If a relatively long collection time is undesirable, the laser power may be increased such that no loss in Raman signal amplitude occurs.

In Raman instruments, interference filters such as notch, bandpass, lowpass, or highpass (for anti-Stokes Raman) filters may be used to prevent excitation light from saturating the sensitive detector. The optical densities of these filters can range from OD4 to OD12 and may be OD6.

Interference filters reflect light outside of the "passband," the band of wavelengths the filter is designed to isolate. As will be further discussed, their performance may be optimized by being tilted away from normal incidence. This tilt may be utilized to collect the amplitude-modulated excitation light reflected or transmitted by the sample, e.g. the diffuse reflectance at the excitation wavelength; the reflected excitation light may be captured by a high speed detector placed off-axis to tilted interference filters.

Intrinsic Raman Spectroscopy

Methods that have been presented for correcting Raman spectra from turbid media have been mostly empirical or functional only in a narrow set of circumstances, such as if only one optical property is variable. Shih et al. derived an expression for Intrinsic Raman spectroscopy using photon migration theory, which is incorporated herein by reference (Shih W C, Bechtel K L, Feld M S. "Intrinsic Raman spectroscopy for quantitative biological spectroscopy, Part I: Theory and simulations", Optics Express, 16(17):12726-12736 (2008)). The primary equation describing the relationship between the intrinsic Raman signal and the measured Raman signal is:

$$Ram_{INT} = \frac{a_x - a_m}{R_{dx} - R_{dm}} \mu_t l.$$

$Ram_{OBS}$ where $Ram_{INT}$ and $Ram_{OBS}$ are the intrinsic and measured (observed) Raman signal, respectively; $R_d$ is the measured diffuse reflectance; a is the albedo ($a=\mu_s/\mu_s+\mu_a$), where $\mu_s$ is the scattering coefficient in $cm^{-1}$ and $\mu_a$ is the absorption coefficient in $cm^{-1}$; the subscripts "x" and "m" refer to the excitation and Raman (emission) wavelengths, respectively; $\mu_t$ the sum of $\mu_s$ and $\mu_a$; and l is the optical path length.

Bechtel et al. demonstrated improved quantification in experiments using a calibrated form of the expression, which is incorporated herein by reference (Bechtel K L, Shih W C, Feld M S. "Intrinsic Raman spectroscopy for quantitative biological spectroscopy, Part II: Experimental applications", Optics Express, 16(17):12737-12745 (2008)). Calibration was necessary because the absolute intensity of the elastically scattered light at the excitation wavelength, $R_{dx}$, was not measured because an interference filter (notch filter) intentionally removed this wavelength prior to the spectrograph in order to prevent scattering in the spectrograph and/or saturating the detector. Further, it was noted in these papers that $\mu_t$ is necessary for correction, but no means for obtaining this was presented. Extraction of optical properties from diffuse reflectance spectra typically relies on a fitting routing that requires the absorption component, $\mu_a$, to have narrow features in order to distinguish it from the elastic scattering component, $\mu_s$. In the near-infrared region known as the diagnostic window there are typically not enough absorption features in tissue to allow for accurate simultaneous fitting of $\mu_a$ and $\mu_s$. Embodiments of the present invention include both algorithmic methods for intrinsic Raman spectroscopy as well as a time-domain experimental methods by which measurement data for intrinsic Raman calculations (or other Raman data) may be obtained.

Figure 2:
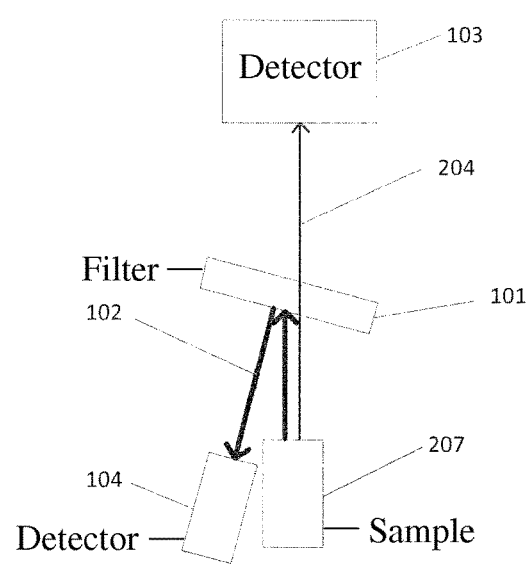
FIG. 2 is a diagram illustrating a configuration by which scattered excitation-wavelength light may be collected from a tilted interference filter in one embodiment of the present invention.

FIG. 2 is a diagram illustrating a manner in which elastically scattered excitation-wavelength light 102 may be collected from tilted interference filter 101. In FIG. 2, excitation-wavelength light 102 has been elastically scattered within sample 207 whereas Raman-scattered light 204 has experienced a frequency (or wavelength) shift by Raman scattering. Raman-scattered light 204 may have a wavelength within the passband of tilted interference filter 101, and therefore passes through the filter and onto detector 103. Elastically scattered excitation-wavelength light 102 may have a wavelength outside of the passband of tilted interference filter 101; it is reflected by tilted interference filter 101 and can be collected by detector 104, placed at an angle from tilted interference filter 101 corresponding to the angle of its tilt. The angle of tilted interference filter 101 may depend on the width of a desirable passband, its type of reflective coating, or other system parameters.

Alternatively, Raman-scattered light and elastically scattered excitation-wavelength light may be collected from spatially offset locations. For example, a detector, possibly with a notch filter excluding excitation-wavelength light, may be located two millimeters away from an excitation source along an arbitrary x-axis, and may detect Raman-scattered light. A detector, possibly filtered to detect only excitation-wavelength light, may be located 1 mm away in the same x-direction, 1 or 2 mm away in the negative x-direction, 1 or 3 mm away along a perpendicular y-axis, directly adjacent to the excitation source, or at any other spatially offset location. Offsetting a detector for the Raman signal can have additional benefits, including increasing the depth of sample from which Raman-scattered light can be detected. Further details of intrinsic, spatially-offset Raman spectroscopy will be provided with an additional embodiment of the present invention.

A signal from captured excitation-wavelength light, e.g. elastically scattered excitation-wavelength light 102, can be processed, e.g. cross-correlated with source modulation sequences, to obtain $TPSF_{EXC}$, the TPSF of the sample at the excitation wavelength. (The optical properties of a sample, and therefore the temporal points spread function of incident photons, may be wavelength-dependent.) Additionally, the intensity of the captured light can be calibrated against or normalized to a reflectance standard, such as the fluoropolymer Spectralon, and serve as the measure of $R_{dx}$, the absolute diffuse reflectance of excitation-wavelength light, or $T_{dx}$, the absolute diffuse transmittance of excitation-wavelength light, depending on whether light was collected in reflection or transmission mode.

A TPSF can be fit to obtain $\mu_a$ and $\mu_s$, the absorption and scattering coefficients respectively, and therefore $\mu_t$, the total attenuation coefficient, at the excitation wavelength. Coefficients $\mu_a$ and $\mu_s$ may be combined (summed) to obtain the total attenuation coefficient $\mu_t$, or can be used individually or in some other combination such as $\mu_s'/\mu_a$ in order to correct the Raman signal. $\mu_s$ can be in its reduced scattering form, $\mu_s'$ ($\mu_s'=\mu_2(1-g)$).

Alternatively, other TPSF metrics may be used for correction of turbidity variations in measured Raman spectra such as width at a given fractional intensity, moments of the distribution, peak height, or peak area. The relationship(s) between a given TPSF metric or metrics and a turbidity correction may be experimentally or analytically determined. Similarly, optical path length information can be used to further quantify the Raman signal. Optical path length information may be determined by the temporal location of the TPSF in a variety of ways, including left edge position, e.g. left edge position 100 in FIG. 1; centroid; first moment of the distribution; or any other means.

A TPSF or optical properties can be used alone or in conjunction with diffuse reflectance or transmittance measured over the same wavelength range as the Raman signal, $R_{dm}$ or $T_{dm}$, or some fraction thereof. If optical properties of the sample do not vary greatly with wavelength, $R_{dx}$ or $T_{dx}$ may be sufficient to correct the Raman signal without aid of $R_{dm}$ or $T_{dm}$, where the subscript "m" again indicates that values correspond to emission wavelengths.

Figure 3:
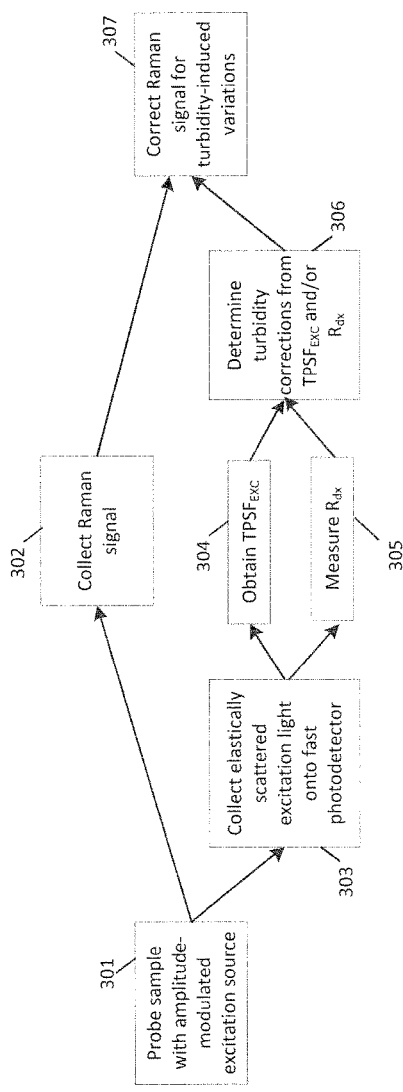
FIG. 3 is a flowchart illustrating an embodiment of the present invention for collecting and interpreting data to achieve intrinsic Raman spectroscopy in the time domain.

FIG. 3 is a flowchart illustrating an embodiment of the present invention as just described for collecting and interpreting data to achieve intrinsic Raman spectroscopy in the time domain. In step 301 an amplitude-modulated excitation source is used to probe, or illuminate, the sample. Amplitude-modulation of the excitation source may be according to predetermined code sequences, e.g. code-modulated. Alternatively, the source may release photons in evenly spaced, sequential pulses without code modulation. Light emitted by the sample with a frequency shift indicative of Raman scattering can be collected in step 302. This light may be focused onto a spectrometer and collected on a CCD or spatially-resolved detector or may be focused into a scanning monochromator and collected on a single-element detector. The detector may be an integrating detector as the intensity and frequency of Raman-scatter light may be of greater interest than its temporal character. Alternatively, the detector may be a fast detector, which can resolve amplitude modulation or determine the temporal character of detected light, and the Raman signal may be integrated over multiple events or code sequences for improved signal-to-noise. Meanwhile, light emerging from the sample with its original wavelength intact, e.g. indicative of elastic scattering, may be collected onto an additional detector in step 303. The additional detector may be a fast photodetector so that $TPSF_{EXC}$ can be determined, as in step 304. $TPSF_{EXC}$ may be obtained by building a histogram of the times between release and detection of photons from the excitation source. If the excitation source is code-modulated, the signal detected in step 303 may be cross-correlated with the predetermined code sequence prior to constructing $TPSF_{EXC}$. Collecting elastically scattered light in step 303 can also serve as a measure of the diffuse reflectance at excitation wavelengths, $R_{dx}$, as indicated by step 305. While $TPSF_{EXC}$ and $R_{dx}$ may correspond to excitation-wavelength light, they can be sufficient for determining appropriate sample turbidity corrections, particularly if the optical properties of the sample do not vary significantly with wavelength. These corrections can be calculated utilizing $TPSF_{EXC}$ and/or $R_{dx}$ in step 306, and can applied to the Raman signal from step 302 in step 307.

Determination of turbidity corrections in step 306 may comprise the calculation of $\mu_a$ or $\mu_s$ from $TPSF_{EXC}$ using a photon diffusion model or other model, comparisons to a family of Monte Carlo-simulated TPSF curves of predetermined optical properties, or any other method. The coefficients $\mu_a$ and $\mu_s$ may be input in an equation relating an intrinsic, e.g. turbidity-corrected, Raman signal with a measured Raman signal. $TPSF_{EXC}$ and $R_{dx}$ may provide sufficient approximations for the temporal point spread function and diffuse reflectance at Raman-scatter wavelengths for use in diffusion-based or other models if the optical properties of the sample do not vary significantly with wavelength.

Alternatively, determination of turbidity corrections in step 306 may comprise extracting a quantifiable TPSF metric, such as the first, second, third, or fourth moment of its distribution; the slope of its rising edge; width at a given fractional intensity; peak height or area; or any other metrics. One or more of these metrics may be associated with a degree or manner of turbidity correction, where a relationship can be determined experimentally or analytically. For example, a relationship may be determined for the embodiment of FIG. 3 by obtaining a Raman signal (as in step 302) and $TPSF_{EXC}$ (as in step 304) for a number of samples with predetermined intrinsic Raman spectra. For each sample, one or a variety of $TPSF_{EXC}$ metrics may be calculated, and differences between the predetermined Raman spectrum and the measured Raman spectrum of step 305 may be compared to calculated $TPSF_{EXC}$ metrics. A relationship between Raman signal corrections and these metrics may be determined, which can be applied to Raman signals of samples whose composition or intrinsic Raman spectra are not predetermined. As a further example, the slope of a tail of a TPSF can be directly proportional to $\mu_a$, so that fitting the tail of $TPSF_{EXC}$ may be used to derive an optical property useful for the absorption component of a turbidity correction.

In a further embodiment of the present invention, a broadband light source positioned collinearly with the excitation laser can be added to the instrument for the purpose of collecting the diffuse reflectance or transmittance at wavelengths which appear in the Raman signal, which may be known or unknown prior to performing Raman spectroscopy of the sample. This embodiment may be particularly useful if optical properties of the sample can vary substantially with wavelength.

Figure 4:
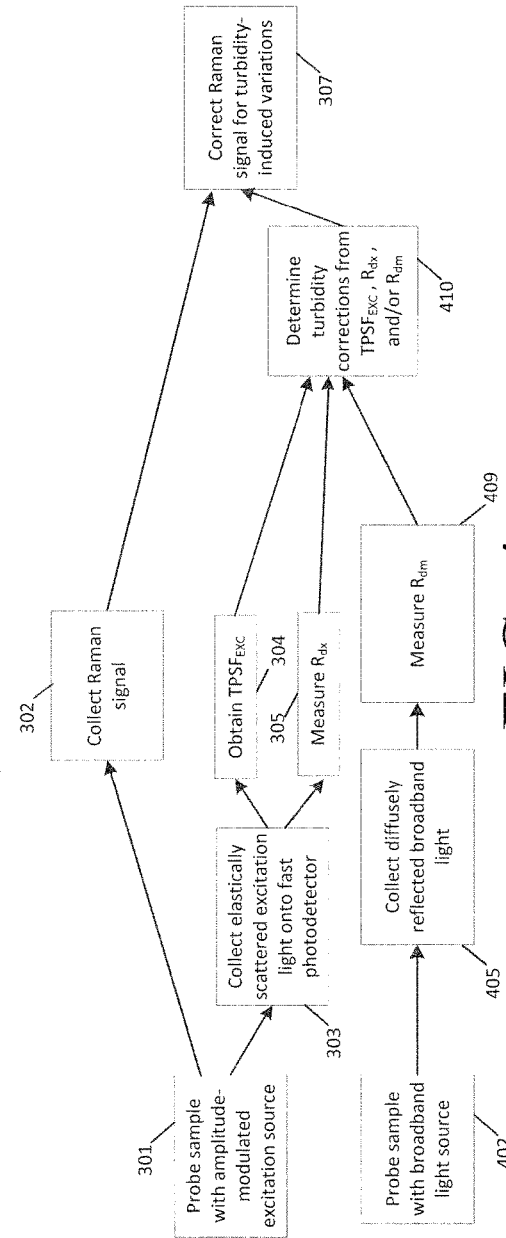
FIG. 4 is a flowchart illustrating an embodiment of the present invention incorporating collection of diffuse reflectance at the Raman emission wavelength using a broadband light source.

FIG. 4 is a flowchart illustrating an embodiment of the present invention incorporating collection of diffuse reflectance at the Raman-emission wavelength using a broadband light source. The embodiment of FIG. 4 follows the time-domain Raman spectroscopy method of the embodiment of FIG. 3. However, in step 402, the sample is probed with a broadband light source, which may emit light with a range of wavelengths including the wavelengths likely to appear in a Raman signal obtained in step 302. Step 405 comprises collecting broadband light scattered, or diffusely reflected, by the sample. Diffusely reflected broadband light may be collected by a spectrometer and CCD detector, scanning monochromator and single-element detector, or any other energy-resolved detection configuration. The detector or detectors may be integrating or fast detectors. Sequential illumination by the excitation source and broadband source along with a flip mirror to re-direct light during one or the other illuminations may allow diffusely reflected broadband light at Raman-scatter wavelengths to be detected separately from Raman-scattered excitation light. Alternatively, spatially separated sources and detectors, or any other means may be used to separate these signals and prevent saturation of the Raman signal with diffusely reflected broadband light.

The diffuse reflectance, $R_{dm}$, can be measured at the Raman-scatter wavelengths in step 405 and step 409. $R_{dm}$ for wavelengths which appear in the Raman signal of step 302 may be utilized for correction of the signal, though diffusely reflected light may be collected over a broader range of wavelengths. Step 410 can comprise determining turbidity corrections from $TPSF_{EXC}$, $R_{dx}$, $R_{dm}$, or some combination thereof. The Raman signal of step 302 can then be corrected for turbidity-induced variations in step 307.

In one embodiment of the present invention, step 410 may utilize the diffuse reflectance at various wavelengths in the Raman signal to determine a correction to the Raman signal. The Raman signal at a given wavelength may be divided by the diffuse reflectance or transmittance at that wavelength, possibly raised to a power determined by an experimental fit, or the Raman signal may be otherwise normalized using the diffuse reflectance or transmittance at Raman emission wavelengths. Dividing or normalizing Raman signals according to diffuse reflectance may serve as a first order turbidity correction of the signal.

Figure 5:
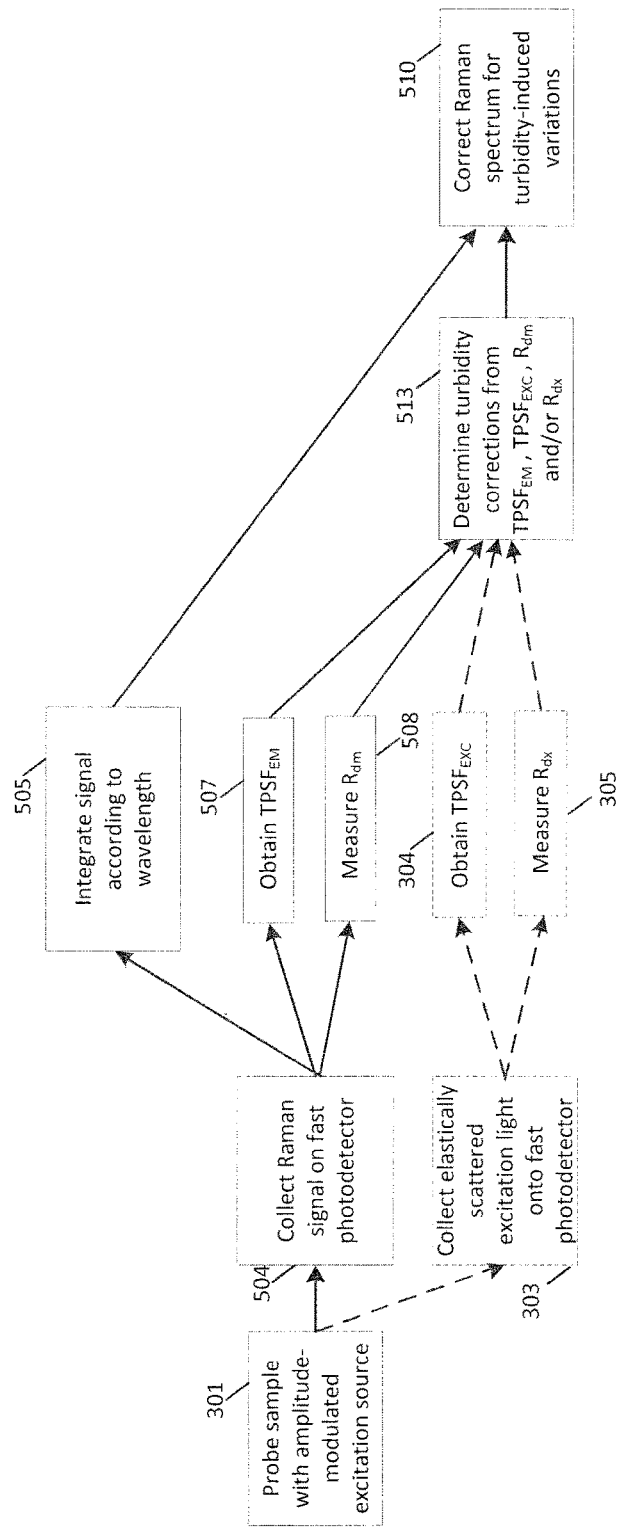
FIG. 5 is a flowchart illustrating a further embodiment of the present invention, which utilizes amplitude modulation of Raman scattered light to obtain TPSF's at each Raman wavelength, thus providing self-correction for optical properties at each wavelength.

FIG. 5 is a flowchart presenting a further time-domain embodiment of the present invention, in which TPSF's can be constructed from Raman-scattered photons and thus provide self-correction for optical properties at wavelengths in a Raman spectrum. This can be realized by utilizing a high-speed detector capable of resolving temporal characteristics of the detected light. As in the embodiments of FIG. 3 and FIG. 4, in step 301 a sample is probed by an amplitude-modulated excitation source, wherein amplitude-modulation may or may not follow a code sequence. In step 504, light which may comprise a Raman signal is collected on a fast photodetector. The fast photodetector may be a single-element detector, and a scanning monochromator, diffraction grating with exit slit, or other means may utilized to trace out the Raman signal at different wavelengths as a function of time.

Since the temporal character of detected Raman scatter can be resolved by a fast photodetector (as utilized in step 504), the TPSF of the Raman signal at each wavelength in a potential Raman spectrum, $TPSF_{EM}$, can be obtained in step 507. $R_{dm}$ can also be measured in step 508 for Raman signal wavelengths collected in step 504. If the excitation source was code modulated, $TPSF_{EM}$ may be obtained by cross-correlating the detected signal with the predetermined source modulation sequence. In this embodiment, a Raman signal, $R_{dm}$, and $TPSF_{EM}$ can be obtained through the same measurement in step 504, resulting in good registration and cost- and time-efficiency. Integration of the signal over multiple events or repeated code sequences may be performed to improve signal-to-noise ratios and construct a Raman spectrum may be completed in step 505.

Obtaining $TPSF_{EM}$ for each Raman signal wavelength may or may not preclude the use of diffuse reflectance or transmittance (intensity information) and $TPSF_{EXC}$ for turbidity correction. Step 513 may comprise determination of turbidity corrections from $TPSF_{EM}$, $TPSF_{EXC}$, $R_{dm}$, and/or $R_{dx}$. A turbidity-corrected Raman spectrum may be generated in step 510.

For example, in step 510 the expression derived by Shih et al relating $Ram_{INT}$ and $Ram_{OBS}$, the intrinsic and measured (observed) Raman signals, $$Ram_{INT} = \frac{a_x - a_m}{R_{dx} - R_{dm}} \mu_t l.$$

$Ram_{OBS}$ may be utilized. In this expression, $R_d$ is the measured diffuse reflectance; a is the albedo ($a = \mu_s / \mu_s + \mu_a$), where $\mu_s$ is the scattering coefficient in cm$^{-1}$ and $\mu_a$ is the absorption coefficient in cm$^{-1}$; the subscripts "x" and "m" refer to the excitation and emission (Raman) wavelengths, respectively; $\mu_t$ is the sum of $\mu_s$ and $\mu_a$; and l is the optical path length. In this embodiment, values of $\mu_a$ and $\mu_s$ may be obtained by analysis of both $TPSF_{EXC}$ (obtained in step 304) and $TPSF_{EM}$ (obtained in step 507) such that $a_x$, $a_m$, and $\mu_t$ can be accurately calculated. As discussed, $R_{dm}$ can be measured through step 504 and step 508, and $R_{dx}$ may be measured through step 303 and step 305. The optical path length, l, may be obtained by analysis of a $TPSF_{EM}$ metric, e.g. left edge position. $Ram_{OBS}$ can be obtained in step 505. Thus, the embodiment of FIG. 5 may provide all measurement values that appear in a photon diffusion model-based, Raman signal turbidity correction.

The expression above or any other expression relating an intrinsic Raman signal to a detected Raman signal may be used. Temporal point spread functions and diffuse reflectance values at both excitation and emission (Raman) wavelengths may be utilized, or only a subset of these values may be utilized for correction of a Raman signal.

While the embodiments of FIG. 3, FIG. 4, and FIG. 5 illustrate time-domain methods of intrinsic Raman spectroscopy, other embodiments of the present invention may utilize spatial- or frequency-domain methods. Similar to the embodiments presented, these embodiments may utilize collection of elastically scattered excitation light, illumination with a collinear broadband light source, or any other means of determining the optical properties of a sample and/or correcting a Raman signal for turbidity-induced variations with good registration.

In one embodiment of the present invention a spatial-domain configuration may be utilized to obtain sufficient data for intrinsic Raman spectroscopy. While in conventional Raman spectroscopy, the Rayleigh line (a possibly large signal from elastically scattered excitation light) may be completely suppressed from a measured Raman spectrum by a notch filter in front of the detector, in this embodiment some portion of the Rayleigh line may be retained and evaluated at a variety of spatially offset positions in order to extract optical properties of a sample. It may be retained as a measurement of $R_{dx}$ and for extraction of further optical properties.

Figure 6:
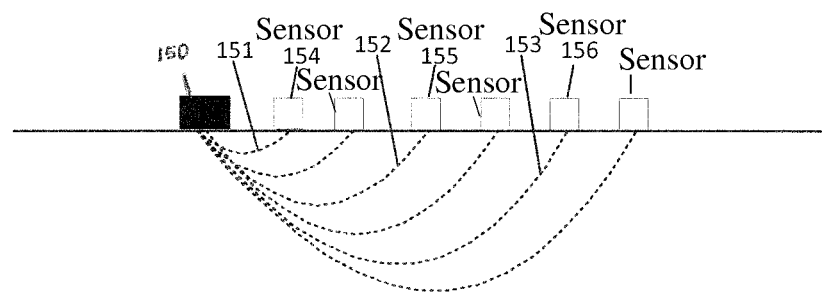
FIG. 6 is a diagram illustrating a source-detector configuration that may be utilized for spatial-domain measurements in one embodiment of the present invention.

FIG. 6 is a diagram illustrating a source-detector configuration that may be utilized for spatial-domain measurements in one embodiment of the present invention. In FIG. 6, source 150 sends photons into a sample, and a number of sensors, including sensor 154, sensor 155, and sensor 156, are positioned at a variety of distances from source 150 to collect photons emitted from the sample. Representative photon paths, such as path 151, path 152, and path 153, are drawn to illustrate the average depth through which photons from source 150 may travel. It can be seen that photons detected by a sensor farther from a source may have penetrated a greater sample depth than those detected by a sensor nearer to a source; photons reaching sensor 156 may have on average followed path 153 whereas photons reaching sensor 154 may have on average followed path 151. A photon travelling a greater distance, e.g. achieving a greater depth, in a turbid medium may interact with a larger number of scattering or absorbing molecules and therefore have a higher probability of being scattered and/or absorbed, which may correlate with a lower probability of returning to the surface of the sample or a sensor. Changes in the Rayleigh line, or peak, across offset spatial locations may be utilized for correction or scaling of Raman signals obtained at those locations. For example, the height or area of the Rayleigh peak at each source-detector separation may be divided by the height or area of the Rayleigh peak of the nearest source-detector separation (presumably the tallest Rayleigh peak), and the Raman signals scaled accordingly. Other Rayleigh peak metrics may be utilized in a similar fashion.

Rayleigh peaks collected across a variety of spatially offset locations, such as by the detector configuration of FIG. 6, may also be fit via diffusion theory-based equations or using Monte Carlo simulations is order to extract optical properties of the sample. For example, it was derived by Farrell et al in "A diffusion theory model of spatially resolved, steady-state diffuse reflectance for the noninvasive determination of tissue optical properties in vivo" that the peak of ln $$\left( r_{SD}^2 \times \frac{R_{SD}}{R_{max}} \right),$$

where $\gamma_{SD}$ is the source-detector separation, $R_{SD}$ is the diffuse reflectance at a given source-detector separation, and $R_{max}$ is the largest diffuse reflectance exhibited by the sample, possibly at the nearest source-detector separation, may be directly proportional to $\mu_s'$. It was also derived that the tail of the above expression may have a slope or derivative proportional to $\mu_{eff}$.

Figure 7:
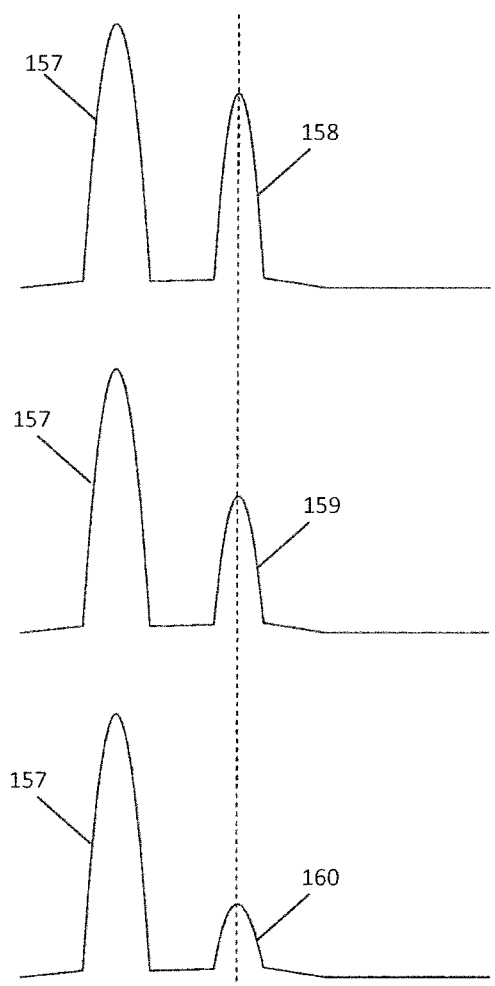
FIG. 7 is a diagram illustrating exemplary Raman signals at a given wavelength for differing source-detector separations.

In an alternative embodiment of the present invention utilizing a spatially offset configuration, e.g. the configuration of FIG. 6, $R_{dm}$ may be determined for Raman-scatter wavelengths by comparing the Raman signal at a given wavelength across multiple spatially offset locations. FIG. 7 is a diagram illustrating exemplary Raman signals at a given wavelength for differing source-detector separations. For example, signal 158 may have been detected by sensor 154, signal 159 from sensor 155, and signal 160 from sensor 156. Signal 160 may be less than signal 159, which may be less than signal 158 due to the previously discussed signal depth-dependence. The relationship between source-detector spacing and signal peak metrics, e.g. height or area, may be utilized to determine $R_{dm}$ at the wavelength of the Raman peak. In FIG. 7, Rayleigh peak 157 appears invariant as the scattering and absorption properties of the sample may be wavelength-dependent. $R_{dm}$ may be similarly determined for other spatially varying peaks in the Raman spectrum.

A variety of source-detector spacing and configurations may be utilized. Detectors may be located along regular or irregular linear intervals from a source, arranged in concentric rings around a source, or in any other configuration. Depending on the application, the number of detectors may be 2, 3, 4, 5, 6, 7, 8, 9, or 10, or any other number up to hundreds. The distances between sources and detectors may be as close as possible given the size of the sensor or detectors, may be larger, or may be smaller if relatively small optical components are attached to sources or detectors. Collection optics, such as 200 µm optical fibers coupled to detectors, may be utilized to increase spatial resolution at the surface of a sample. Detectors, or fibers, may be positioned any distance between 100 µm to 2 cm away from a source. Alternatively, detectors may be positioned between 1 to 3 mm or 1 to 4 mm away from a source, or up to 1 cm away from a source. In one embodiment of the present invention, 200 µm optical fibers are positioned in concentric rings of radii 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, and/or 4 mm.

Swept-Source Raman Spectroscopy

Embodiments of the present invention provide new implementations of Raman spectroscopy that utilize a fixed-wavelength detector or detectors and a frequency-swept source or sources. In these embodiments, a Raman spectrum or subset thereof may be traced out as a function of time. As an excitation source is swept across a range of frequencies, the difference between the frequency (or wavelength) of excitation light and the wavelength to which a fixed-wavelength detector is sensitive can correspond to frequency shifts induced by Raman scatter, e.g. to the x-axis of a Raman spectrum. Embodiments of the present invention utilizing a swept source may be implemented with time-domain, e.g. amplitude modulation of excitation light, spatial-domain, e.g. spatially offset sensors, or frequency-domain measurement techniques.

Figure 8:
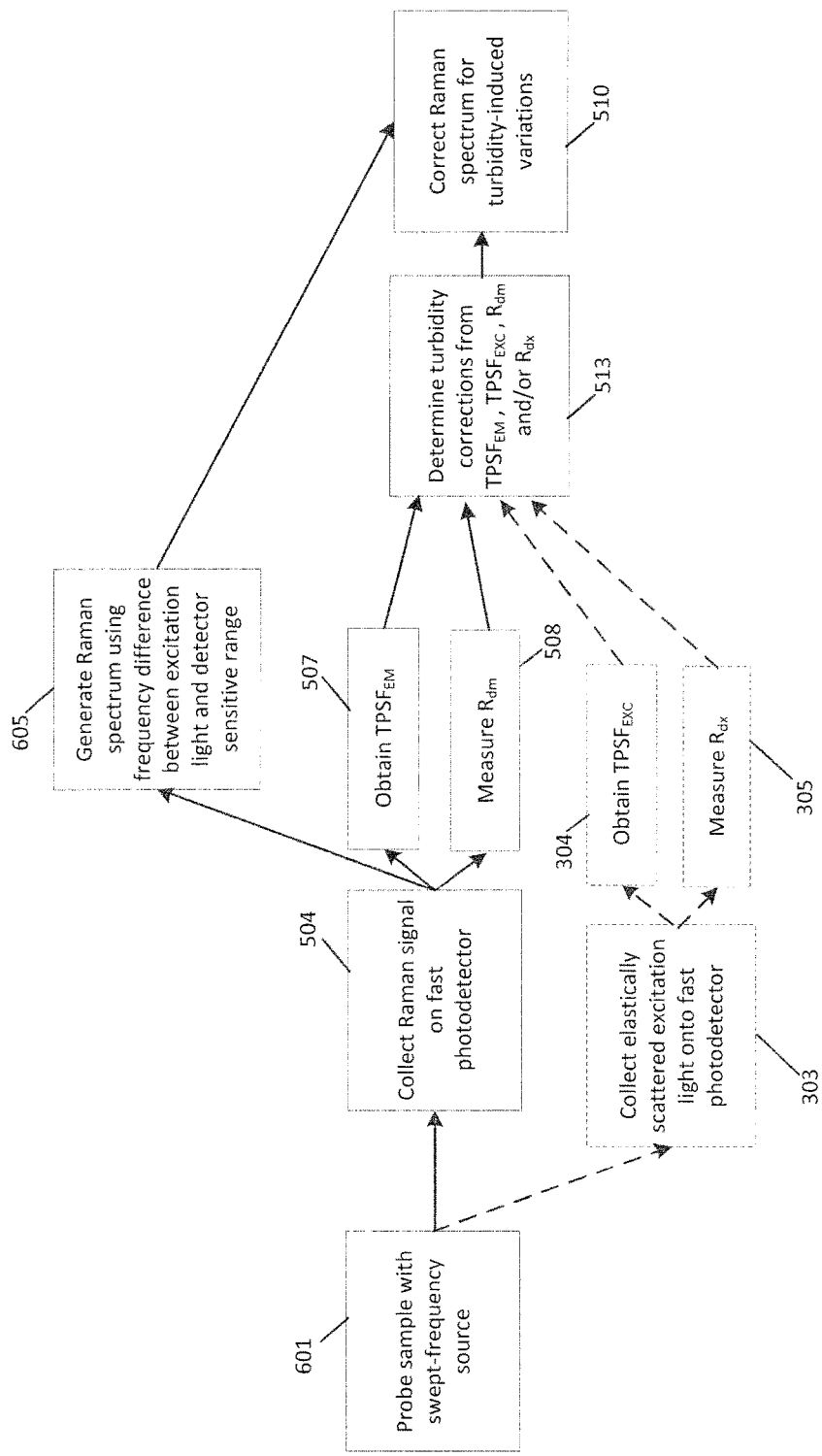
FIG. 8 is a flowchart illustrating an embodiment of the present invention comprising time-domain, swept-source Raman spectroscopy.

FIG. 8 is a flowchart illustrating an embodiment of the present invention comprising time-domain, swept-source Raman spectroscopy. A Raman signal from the sample may be collected on a fast photodetector in step 504. While step 504 in the embodiment of FIG. 5 may require the Raman signal to be passed through a scanning monochromator or similar configuration prior to detection, in this embodiment light may be focused onto a detector measuring a single wavelength or narrow band of wavelengths, as the frequency shift being measured can be determined directly by the difference between excitation light and detection sensitivity. The wavelength or wavelengths detected may be determined by the detector type and material or by a narrowband filter placed in front of the detector. For example, if a detector is sensitive (either inherently or by filtering) to 1000 nm light and a sample has a vibrational mode which can decrease the wavelength of excitation light by 100 nm via Raman scattering, a relatively large Raman signal may appear as an excitation source sweeps through 1100 nm. Since the sensitivity of a detector, e.g. 1000 nm, and the time dependence of the source sweep, e.g. the times at which 1100 nm and other wavelengths are utilized, the Raman signal can be correctly mapped to wavelength shifts as a function of time. While wavelengths are here used for simplicity of explanation, Raman shifts may instead be measured or reported in frequencies or wavenumbers.

The excitation source can be swept over a range of frequencies in step 601 in order to trace out the Raman spectrum on the detector as a function of time, and a Raman spectrum can be constructed as previously described in step 605.

Step 507 and step 508 can be completed as in the embodiment of FIG. 5, such that $TPSF_{EM}$ and $R_{dm}$ may be used to calculate turbidity corrections in step 513 and used to correct the Raman spectrum in step 510. Optionally, step 303, step 304, and step 305 may be completed such that $TPSF_{EXC}$ and $R_{dx}$ can also be used to correct the Raman spectrum in step 513 and to correct the Raman spectrum in step 510.

As mentioned above, it can be seen that the swept-source embodiment of FIG. 8 shares the advantage of the embodiment of FIG. 5 for intrinsic Raman spectroscopy—data sufficient both to construct a Raman spectrum and obtain $TPSF_{EM}$ at Raman wavelengths can be obtained in the same measurement, e.g. by use of a single fast photodetector. However, the swept-source embodiment of FIG. 8 can also eliminate the slit and diffraction grating, or scanning monochromators, that may be required by the embodiment of FIG. 5 and dispersive Raman systems as well as the interferometer required in FT-Raman systems. While swept-source embodiments may not possess the multiplex or multichannel advantage, they can have higher optical throughput by not requiring slits, utilizing fewer optical elements, and having reduced collimation requirements. These embodiments may also be more cost effective.

Furthermore, embodiments of the present invention can be miniaturized, possibly by use of a MEMS scanning laser, and readily allow for cost-effective long-wavelength Raman and code modulation. Code-modulated Raman may require a detector that can respond at speeds up to several GHz; while imaging or array detectors may not respond at such speeds, a fast photodetector as is utilized in embodiments of the present invention can respond at those speeds.

A further advantage of embodiments of the present invention may be that system performance parameters can be optimized for particular applications. For example, for analysis of complex mixtures, high spectral (frequency) resolution may be needed, in which case relatively narrow, e.g. 10 to 30 $cm^{-1}$, band filters can be utilized. In embodiments of the present invention particularly suited to analyses requiring high spectral resolution, narrowband filters may be utilize with frequency resolutions of 4 $cm^{-1}$, 4 to 10 $cm^{-1}$, 10 to 15 cm$^{-1}$, 15 to 20 cm$^{-1}$, 20 to 25 cm$^{-1}$, 25 to 30 cm$^{-1}$, or 30 to 35 cm$^{-1}$. On the other hand, for monitoring of a single analyte, as may be done in process monitoring, the frequency resolution of the band filter can be wider, e.g. 30 to 100 cm$^{-1}$, to include an entire particular Raman line, resulting in an increase in signal-to-noise ratio per unit time. In embodiments of the present invention particularly suited to analyses where improved signal-to-noise may be more useful than high spectral resolution, broader band filters may be utilize with frequency resolutions of 30 cm$^{-1}$, 30 to 40 cm$^{-1}$, 40 to 50 cm$^{-1}$, 50 to 60 cm$^{-1}$, 60 to 70 cm$^{-1}$, 70 to 80 cm$^{-1}$, 80 to 90 cm$^{-1}$, 90 to 100 cm$^{-1}$, or greater than 100 cm$^{-1}$.

The resolution of a detected Raman spectrum may be set by the bandwidth, i.e. the number of frequencies within the passband, of the bandpass filter in a swept-source Raman system if the swept excitation source has a narrower instantaneous linewidth, i.e. if the range of frequencies within light emitted from the source at a given instant is smaller than range permitted by the filter passband. For example, the instantaneous linewidth of some rapidly-swept lasers can be quite narrow, e.g. corresponding to less than 1 cm$^{-1}$. Thus the frequency increments by which a source is swept may be less than 1 cm$^{-1}$. Alternatively, larger frequency increments may be utilized. For example, a 1 cm$^{-1}$, 2 cm$^{-1}$, 3 cm$^{-1}$, or any other integer or non-integer frequency increment less than or greater than 1 cm$^{-1}$ may be utilized.

For Raman spectroscopy, resolution better (i.e. less) than 30 cm$^{-1}$ may be preferable, although for specific applications the resolution may be much worse (i.e. greater) than 30 cm$^{-1}$. Raman-generated spectral resolutions may range from 4 cm$^{-1}$ to 12 cm$^{-1}$, but for high-throughput dispersive Raman systems may range from 12 cm$^{-1}$ to 30 cm$^{-1}$.

One type of bandpass filter that may be used in embodiments of the present invention is an interference bandpass filter. Interference filters utilize two outer semi-reflective layers and an inner layer of known refractive index such that one or multiple internal reflections may occur within the inner layer, and the phases of light which escapes the filter at each point of reflection may interfere constructively for desired frequencies and destructively for undesired frequencies. As the response from interference filters can depend on angles of incidence, the bandwidth created by filtering can be reduced by using two such filters and angle-tuning with respect to one another. Rotation of an interference filter may shift the passband to shorter wavelengths. By tilting one of the interference filters with respect to the other, the passband of the tilted filter may only partially overlap the passband of the fixed filter. Thus, the combined passband can be made narrower. Tilt angles can range from zero to eighty degrees and can be any integer or non-integer value between zero to eighty degrees. Further, two, three, four, or more filters may be tilted in conjunction with one another to further optimize the combined passband. The use of multiple interference filters can have the added advantage of further reducing the intensity of the excitation source wavelength(s) on the detector, potentially improving the signal-to-noise ratio of detected Raman scattered light.

Besides dielectric interference filters, other methods of ensuring that the detector measures only a single wavelength or narrow band of wavelengths may be used, including but not limited to: tunable filters in a variety of configurations; Fabry-Perot filters, also known as etalons; absorption filters; and prisms or gratings, reflective or holographic, in combination with a spatial selector such as an aperture or slit.

The range of Raman-scatter frequencies that can be collected can be determined by the sweep range of the excitation source. Modern lasers can be swept over a large wavelength range, e.g. 70 to 180 nm, very quickly, with speeds ranging from kHz to MHz. In embodiments of the present invention, an excitation source may be swept at any speed manually, automatically, using feedback loops, or in any other manner. A source may be swept through a range of wavelengths or frequencies at a speed of 10 kHz, 20 kHz, 30 kHz, 40 kHz, 50 kHz, or any integer or non-integer speed between these enumerated speeds. Alternatively, the source may be swept at any speed between 0 and 1 MHz, as the laser or excitation source allows.

The sweep of a laser or excitation source can be centered at any wavelength from 700 nm to 2.5 μm. The sweep range can be any range from 1 nm to 1500 nm. Expressed in wavenumbers, sources may be swept across ranges that may be between 1 and 4000 cm$^{-1}$, between 200 and 2000 cm$^{-1}$, between 500 and 1800 cm$^{-1}$, between 2750 and 3400 cm$^{-1}$, or any combination or subset thereof, and therefore measure Raman shifts across these ranges. Alternatively, a source may be swept over a relatively narrow range in order to measure a single Raman peak or other narrow subset of a Raman spectrum. For example, a source may be swept across a range of 4 cm$^{-1}$, 10 cm$^{-1}$, 11 cm$^{-1}$, 12 cm$^{-1}$, 30 cm$^{-1}$, or any other number of wavenumbers which may encompass a Raman peak. A sweep across 4 cm$^{-1}$ may be utilized to measure a relatively sharp Raman peak, across 10 to 12 cm$^{-1}$ an average Raman peak, and up to 30 cm$^{-1}$ or above a relatively broad Raman peak.

The detector can be filtered to measure any wavelength from 700 nm to 2.5 μm with frequency resolutions of 1 to 4000 cm$^{-1}$.

One embodiment of the present invention comprises a swept source with a detector that measures at 1535 nm+/−1.5 nm with the aid of a narrowband interference filter placed in front of the detector. In this embodiment the excitation source may be a frequency-swept laser centered at 1290 nm with a 160 nm bandwidth. Therefore, the laser can sweep from 1210 nm to 1370 nm, which corresponds to a frequency difference between the laser and the fixed-wavelength detector at 1535 nm of 1750 cm$^{-1}$ to 785 cm$^{-1}$, covering the Raman spectral range of interest for many applications. Thus, by examining the detector output, the Raman spectrum can be traced out as a function of time.

Other lasers may be utilized that cover wider or narrower ranges around the same or different center wavelengths. Similarly, other filters and detector combinations may be used that are centered at different wavelengths.

Another embodiment of the present invention utilizes a swept-source laser with center frequency 1050 nm and sweep range 150 nm. Two narrowband interference filters are used to allow only 1182 nm+/−1 nm onto the detector. This swept range corresponds to Raman frequencies of approximately 430 to 1800 cm$^{-1}$, with frequency resolution of approximately 14.5 cm$^{-1}$.

Embodiments of the invention can be suitable for any wavelength, from the ultraviolet to the infrared. Particular usefulness may be noted for the near-infrared region, i.e. above 900 nm range, for dispersive Raman spectroscopy suffers from lack of a low-cost, low-noise, high-sensitivity detector array.

As previously mentioned, embodiments of the present invention utilizing a swept source may be well-suited to code-modulated Raman spectroscopy. In one embodiment of the present invention, an excitation source is frequency swept at a low enough rate (e.g. slowly enough) for the source to undergo modulation by one full code sequence at each frequency increment of the sweep. For example, the excitation source may be modulated at 1 GHz such that one full code sequence may be emitted in approximately 1 μs (greater detail regarding code sequences is provided in the following section, "Exemplary code modulation"). At such a modulation rate, the excitation source may be frequency swept at a rate of 1 MHz or less to allow modulation according to one full code sequence at each frequency increment. Alternatively, the excitation source may be frequency swept more slowly to allow multiple code sequences of modulation at each frequency increment. For example, the excitation source may be frequency swept at 0.5 MHz or less to allow the source to be modulated by two sequential code sequences at each frequency increment, 0.33 MHz or less to allow the source to be modulated by three sequential code sequences at each frequency increment, 0.25 MHz or less to allow the source to be modulated by four sequential code sequences at each frequency increment, and so forth. Integration of a detected Raman signal over multiple code sequences may improve the signal-to-noise ratio of resultant Raman spectra. Furthermore, code modulation of the excitation source may increase the speed of data collection, lowering the integration time necessary to build up adequate signal-to-noise histograms for accurately fitting a TPSF.

Figure 9:
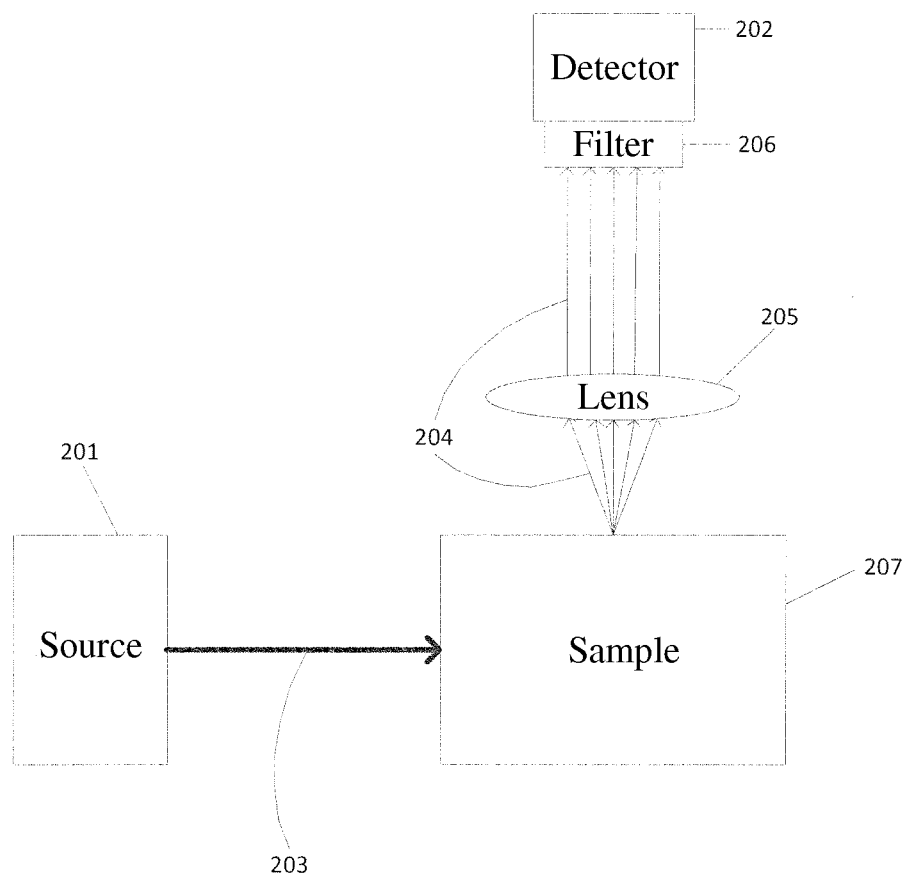
FIG. 9 is a diagram illustrating one embodiment of the present invention utilizing free-space excitation and collection optics in which a swept source and a detector are positioned with perpendicular angles of incidence.
Figure 10:
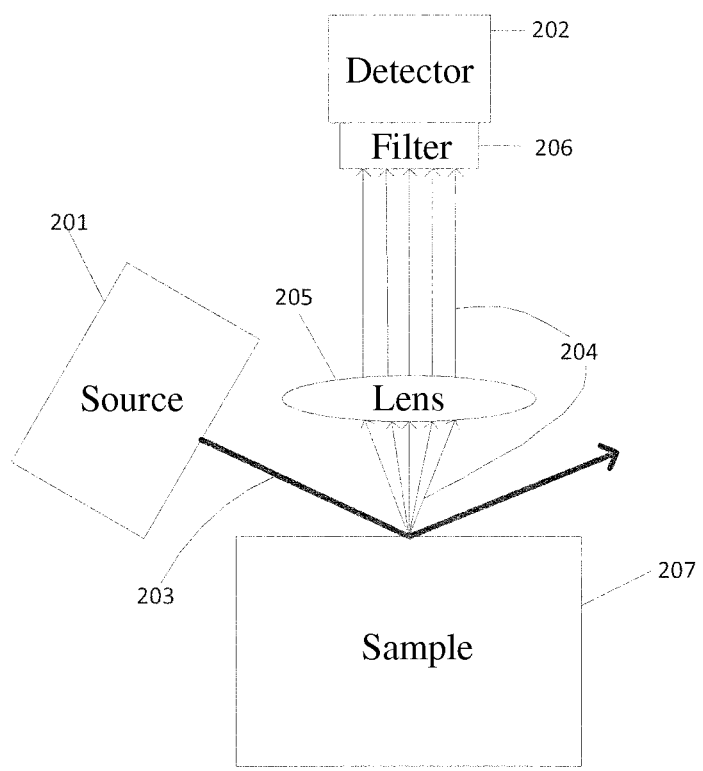
FIG. 10 is a diagram illustrating an embodiment of the present invention in which a swept source and a detector are positioned such that their angles of incidence with a sample form an acute angle.

FIG. 9 is a diagram illustrating one embodiment of the present invention that utilizes free-space excitation and collection optics, in which swept source 201 and detector 202 are placed such that their angles of incidence with sample 207 are perpendicular to one another. FIG. 10 is a diagram illustrating a similar embodiment, the difference being an acute angle formed by the angles of incidence of swept source 201 and detector 202. Note that excitation light 203 may be delivered by free-space optics, fiber optics, other optical delivery methods, or some combination thereof. Similarly, Raman scattered light 204 may be collected by free-space optics, fiber optics, other optical delivery methods, or some combination thereof. In the embodiments of FIG. 9 and FIG. 10, Raman scattered light is collected by one or more single or multi-element lenses 205, passed through one, two, or three interference filters 206, and focused onto a single- or multi-element detector 202.

Excitation sources that may be used for fixed-frequency Raman spectroscopy, e.g. for the embodiments of FIG. 3, FIG. 4, and FIG. 5, include gas lasers, such as $Ar^+$ lasers and other gas lasers; solid state lasers, such as diode lasers, external cavity diode lasers for added frequency stability, and other solid state lasers; or any other type of light sources. Excitation sources for swept-source Raman spectroscopy, e.g. for the embodiment of FIG. 6, may be external cavity diode lasers or other light sources. Frequency sweeping can be performed within the laser cavity by rotating a diffraction grating, a diffraction grating and mirror, or by any other means.

Embodiments of the present invention may utilize a balanced detector, wherein a small amount of excitation light hits one of the elements, which measures a different frequency of light than other element(s), and is used to correct for intensity variations in the light source. Alternatively, two single element detectors can be used, wherein one single-element detector is used to measure the Raman light passing through the interference or other bandpass filter and a separate, second single-element detector is used to measure the excitation light reflected off of the interference filter. The electronics for the multiple detectors may be individual or combined in a fashion to perform automated subtraction or ratio determination.

The detector material of a detector or detectors utilized in embodiments of the present invention may be silicon, InGaAs, InAs, Ge, Ge deposited on Si, or "black silicon." Detector types may be PIN, APD, or PMT and either cooled (by thermoelectric, air, water, liquid nitrogen, or liquid helium) or uncooled. Each detector may be a single-element detector, pixilated detector, array detector, CCD, or any other type of detector.

Figure 11:
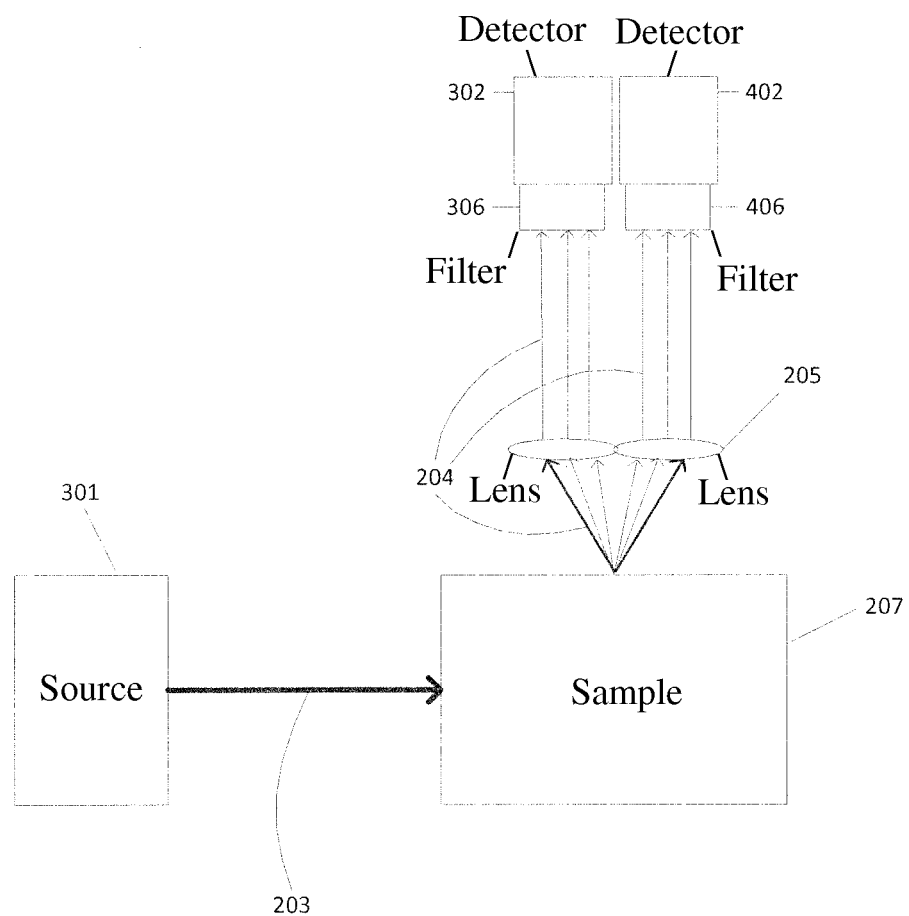
FIG. 11 is a diagram illustrating an embodiment of the present invention in which two detectors are utilized in place of a swept source.

FIG. 11 is a diagram illustrating an embodiment of the present invention in which two detectors are utilized in place of a swept source. In this embodiment, Raman light 204 collected from the sample of interest can be focused onto two detector elements, each of which can be filtered to detect a unique passband. Excitation light 203 may be delivered by free-space optics, fiber optics, other optical delivery methods, or some combination thereof. Detector 302 can measure a first wavelength, within a passband given by filter 306, and detector 402 can measures a second wavelength, within a passband given by 406. Excitation source 301 can emit light of a fixed frequency rather than being a swept source. The different passbands of filter 306 and filter 406 can allow detector 302 to measure one Raman frequency and detector 402 to measure a second Raman frequency.

The two different Raman frequencies measured by detector 302 and detector 402 may correspond to the frequency positions of two different peaks of a particular analyte or mixture signal of interest. For example, in one embodiment of the present invention, the peaks correspond to carbonate and phosphate in the Raman spectrum of bone or of bone underlying tissue. The signals measured from detector 302 and detector 402 may be compared in a fashion to determine characteristics of the bone material, including fracture risk.

Alternatively, excitation source 301 may be swept over a small frequency region corresponding to only the Raman peaks of interest. This method may be particularly useful if only one or a few Raman peak(s) are of interest. In further embodiments of the present invention, a number of detectors attached to a number of filters corresponding to the number of peak(s) of interest may be used.

In another embodiment of the present invention, the source may be swept according to two components; the instantaneous source wavelength may be the sum of a component linear in time and a component sinusoidal in time. The sinusoidal component may be chosen to have an amplitude, reported in wavelength or wave number, that is comparable to or smaller than the typical width Raman lines to be measured, e.g. 4 $cm^{-1}$ or less. In this embodiment, the signal from the detector may comprise a sweep, corresponding to the linear component, through the derivative of the Raman spectrum, arising from the sinusoidal part; the sinusoidal component of the source may result in a sinusoidal response, wherein the amplitude of the sinusoidal response corresponds to the derivative of the Raman spectrum. Binning or averaging this fast sinusoidal response along the linear component, i.e. along a wavenumber axis as the source is swept linearly through increasing wavenumbers, can translate the detected signal into a plot of wavenumber verse signal derivative. Because the Raman spectrum often comprises relatively narrow resonance lines on a smoothly varying background, taking the derivative of the spectrum can emphasize the Raman lines and minimize the impact of any slowly-varying background that may be present. As a derivative may change signs, e.g. from positive to negative, at the tip of a spectral peak, peaks in a Raman spectrum may appear as x-axis intersections in this embodiment of the present invention, further simplifying the extraction of exact peak locations.

The detected signal may be further processed in a manner to display the second derivative or second harmonic of the signal verse wavenumber. While the first derivative of the signal may be particularly useful for extracting precise Raman peak locations out of a slowly varying background, a second derivative of the signal may be particularly useful for extracting linewidth, or Raman peak-width, information against said background; a second derivative may indicate the location and strength of inflection points, which can be related to the width of a peak.

In a further example of this embodiment, the sinusoidal modulation of the source allows the source to be "locked" to a particular Raman line, which would allow the use of a less stable and less expensive swept source. For this embodiment, the uppermost section of a peak in a Raman signal may be utilized. The peak section can be small enough, or "zoomed in" enough, that the y-axis dependence on x is quadratic, e.g. $y=-x^2$, and the x-coordinates can be temporarily redefined such that the peak section is centered, or maximized, at zero. It may be noted that, according to Taylor's theorem, a section of a Raman peak may always be found which can be modeled by a quadratic function. An excitation source may be swept with a sinusoidal time dependence, e.g. $x=\sin(\omega \cdot t)$. If the source is centered precisely such that the difference between its center excitation wavelength and the wavelength measured by a detector is equal to the center of the above described Raman peak, then the Raman signal on the detector may be $y=-(\sin(\omega \cdot t))^2=-\frac{1}{2}+\frac{1}{2}\cos(2\omega \cdot t)$. It can be seen that the detected Raman signal when the source is precisely centered on a Raman peak and swept sinusoidally is also a sinusoid, plus a constant (or, specifically, the second harmonic of the sinusoid of the sweep).

In comparison, if the source were swept with the same sinusoidal time dependence but centered with some offset, "a," from the center of the Raman peak, e.g. $x=a+\sin(\omega \cdot t)$, then the detector response may be $y=-(a+\sin(\omega \cdot t))^2=\frac{1}{2}(\cos(2\omega \cdot t)-4 a \sin(\omega \cdot t)-2 a^2-1)$. In this signal, the sinusoidal component of the source sweep is present, multiplied by the offset: $y_1=a\cdot \sin(\omega \cdot t)$. It can be seen that for zero offset, e.g. a well-centered sweep, this first harmonic term will not exist in the signal, and that the signal may be represented by the previous expression, $y=-\frac{1}{2}+\frac{1}{2}\cos(2\omega \cdot t)$. However, for an off-center sweep, the harmonic $y_1=a\cdot \sin(\omega \cdot t)$ may be detected in the signal as the source is swept, and can be analyzed to determine "a." Thus, it can be determined from the sign and magnitude of the signal amplitude both which side of and how far from the center of a Raman peak the source is being swept. This information may be utilized to manually adjust the sweep center to precisely locate Raman peaks, may be incorporated into a feedback loop wherein a system can be "locked" to a particular Raman peak, or may be utilized in any other manner.

In yet another example of this embodiment, when the source is thus "locked" to a particular Raman line, the second harmonic, e.g. the Raman signal amplitude $y=J\frac{1}{2}+\frac{1}{2}\cos(2\omega \cdot t)$, of the sinusoidal source modulation can be analyzed for information about the amplitude and width of the Raman peak, which information can be useful for inferring additional information, such as the amount of the particular substance being analyzed.

It may be noted that probing the derivate(s) of a Raman spectrum, "locking" to a Raman peak as described, and other measurement techniques utilizing a sinusoidal source component and fast signal response may be difficult or impossible within conventional methods of Raman spectroscopy whereas swept-source embodiments of the present invention can be adapted for them.

The sample of interest on which Raman spectroscopy may be performed using embodiments of the present invention may be human or animal tissues, chemicals, pharmaceuticals, plastics, or other materials. The number of detectors or detector elements may be one, two, up to ten or twenty, or any other number.

In another embodiment, a single detector with a filter or filters corresponding to a single narrow-band wavelength region measures the Raman signal from two or more excitation sources at fixed frequencies. The excitation sources may be alternately turned on and off in order to measure two or more different Raman frequencies. Alternatively, the excitation sources may be modulated over a narrow frequency range to cover the peaks of interest. Further, the excitation sources may be amplitude-modulated using various codes such as Golay, Galois, Gold, Kasami, or pseudo-random binary sequences (PRBS) and the detector signal demodulated, e.g. cross-correlated with the excitation source modulation sequence, to recover the information for the Raman frequencies of interest.

In another embodiment of the present invention, the excitation source(s) may be amplitude- or frequency-modulated and the detected Raman light demodulated to obtain the temporal point-spread function (TPSF) of the sample at each Raman frequency. The excitation light reflected from interference signal can be detected by a second detector and demodulated in order to obtain the TPSF at the excitation frequency(ies).

Exemplary Code Modulation

Under one embodiment of the present invention, the chosen code sequence for code modulation of an excitation source, e.g. swept source 201, is a unipolar code sequence. A digital modulation signal can be transmitted to the excitation source or can be used with an external modulator or electro-optic modulator with the excitation source. A unipolar code sequence allows for the use of commercially available continuous wave lasers or light emitting diodes (LED's) as an excitation source. A bipolar code sequence may not allow for the use of commercially available continuous wave lasers or LED's as a light source because a bipolar code sequence requires the transmission of −1's or negative states. With commercially available continuous wave lasers or LED's, −1's or negative states are difficult to achieve. In addition, the chosen code sequence of for digital modulation of an excitation source can be a code sequence where the autocorrelation is orthogonal. An orthogonal code sequence can result in a correlation which is flat or relatively flat away from both sides of the peak and can make the processing and analysis for the temporal transfer characteristic or the temporal point spread function easier as well as reducing errors. This characteristic also allows for simultaneous transmission of multiple code sequences and analysis of the multiple code sequences without interference from each code sequence.

Under another embodiment, the chosen code sequence for modulation of an excitation source is a code sequence with high autocorrelation approaching the delta function and low cross-correlation values. The chosen code sequence can be an Optical Orthogonal Code. Two codes of length N=36 or 36 elements can be used, 110100010000000000000000000000000000 and 100001000000010000000000010000000. The maximum autocorrelation value is 4 and the maximum cross-correlation value is 1. The ratio of the maximum autocorrelation value to maximum cross-correlation value is 4. However, Optical Orthogonal Codes generally have many more 0's (or low states) than 1's (or high states) making them difficult to implement with commercially available continuous wave lasers or LEDs. In addition, the relatively high cross-correlation values hinder the processing and analysis for the temporal transfer characteristic or the temporal point spread function and can introduce errors.

Under another embodiment, the chosen code sequence for modulation of an excitation source comprises individual code elements where the individual code elements have a length of one nanosecond. Alternatively, individual code element lengths of 25 ps, 50 ps, 75 ps, 100 ps, 125 ps, 150 ps, 175 ps, 200 ps, 250 ps, 500 ps, 750 ps, 1 ns, 1.5 ns, 2 ns, 2.5 ns, 3 ns, 4 ns, 5 ns, 6 ns, 7 ns, 8 ns, 9 ns, 10 ns, 11 ns, 12 ns, 13 ns, 14 ns, 15 ns, 16 ns, 17 ns, 18 ns, 19 ns, 20 ns or any length in between such lengths or any range of lengths in between 25 ps and 20 ns could be used. Individual code element lengths that are longer allow the use of slower and less expensive lasers or LEDs as excitation sources. However, the amount of time to transmit and process the chosen code sequence is dependent on the individual code element lengths multiplied by the number code elements in each sequence. In addition, the width of the temporal transfer characteristic or the temporal point spread function can be as narrow as one nanosecond or less. For narrow temporal transfer characteristics or the temporal point spread functions, a long code element length would lack adequate resolution to properly derive the temporal transfer characteristic or the temporal point spread function.

Under another embodiment, multiple code sequences of 2, 3, 4, 5, 6, 7, 8, 9, 10, 20, 30, 40, 50, 60, 70, 80, 90, 100, 1,000, 10,000, 100,000, 1,000,000 code sequences or any code sequence in between such code sequences or any range of code sequences in between 2 and 1,000,000 code sequences can be used and correlation performed on averaged data or average performed on correlations of data. The multiple code sequences can be multiple identical code sequences. Use of multiple code sequences may allow the averaging out of noise effects, improvement of signal-to-noise ratio, or averaging out of temporary deviations in the system or the sample prior to stabilization of a Raman system. However, a long individual code element length can result in long processing time particularly for high number of code elements in each sequence and particularly if a large number of multiple code sequences is utilized.

Under another embodiment, the chosen code for modulation of an excitation source is a code sequence from the Golay class of codes. Golay codes are bipolar making them difficult to use with commercially available continuous wave lasers or LEDs as a light source. However, in this embodiment, the bipolar Golay code sequence is converted into two unipolar code sequences. For example, a bipolar code sequence represented by A(t) can take on values 1 and −1. Two unipolar code sequences UA1(t) and UA2(t) can be constructed where UA1(t)=½[1+A(t)] and UA2(t)=½[1−A(t)].

In addition, complementary Golay codes can be used where the sum of the autocorrelations is a delta function with the maximum autocorrelation value equal to N where N is the length of the code sequence or the number of individual code elements in the code sequence. In this example, the bipolar code sequence represented by A(t) can be converted to two unipolar code sequences UA1(t) and UA2(t) where UA1(t)=½[1+A(t)] and UA2(t)=½[1−A(t)]. The complementary bipolar code sequence represented by B(t) can be converted to two unipolar code sequences UB1(t) and UB2(t) where UB1(t)=½[1+B(t)] and UB2(t)=½[1−B(t)]. Four code sequences UA1(t), UA2(t), UB1(t) and UB2(t) would be used to drive optical illumination source 3. Four readout traces could be obtained RA1(t)=UA1(t)*f(t), RA2(t)=UA2(t)*f(t), RB1(t)=UB1(t)*f(t), and RB2(t)=UB2(t)*f(t). The temporal transfer characteristic or the temporal point spread function can be obtained by performing the following calculation: fest=A(t)·[RA1(t)−RA2(t)]+B(t)·[RA1(t)−RA2(t)]. Using the four unipolar code sequences has the advantage that commercially available continuous wave lasers or LEDs can be utilized as an excitation source. In addition, the sum of the autocorrelations approaches a delta function where width is related to code element length, making it easier to derive the temporal transfer characteristic or the temporal point spread function. However, using four code sequences has the disadvantage that longer transmission time and longer processing time is required. If an excitation source is unstable or exhibits amplitude variations or different DC biases, errors can be introduced in processing and processing can be more difficult. In addition, because each code sequence can result in a different DC bias and an excitation source may require a period of stabilization during each code sequence, the stabilization would introduce additional transmission time and processing time for each code sequence.

Under another embodiment, the chosen code sequence for modulation of an excitation source is a code sequence from the Galois class of codes. Galois codes do not have ideal autocorrelation but the autocorrelation is uniform on both sides of the peak. The uniformity allows for better or enhanced noise processing and enhanced ability to derive the temporal transfer characteristic and the temporal point spread function. Galois codes have the advantage that it can be implemented with a single unipolar code sequence. The single unipolar code sequence may make a Raman system less susceptible to instability, amplitude variations or differing DC biases in the excitation source. In addition, to the extent optical illumination source 3 may require a period of stabilization during each code sequence, the stabilization time would have less of an impact on transmission time and processing time. A chosen code sequence using a code sequence from the Galois class of codes has a circular autocorrelation of N or approaching N near the peak and −1 or approaching −1 away from the peak, where N is the length of the code sequence or the number of individual code elements in the code sequence. The ratio of the maximum circular autocorrelation value to maximum cross-correlation value is N. A circular code sequence has the important feature that the circular autocorrelation can begin at any point or any code element. The phase of the code sequence does not need to be tracked. A chosen code sequence using a code sequence from the Galois class of codes can have 31, 63, 127, 255, 511, 1023, 2047, 4095 and 8191 individual code elements in the code sequence.

Under another embodiment, the chosen code sequence for modulation of an excitation source is a linear-feedback shift-register sequence, in particular a maximal-length sequence or m-sequence. An n-bit shift register can encode $2^{n-1}$ states, so an m-sequence or maximal-length sequence can have $2^{n-1}$ elements before repeating. All zeros in the shift register is a fixed-point unto itself so it cannot be part of any sequence longer than $2^{n-1}$. Maximal-length sequences or m-sequences have one more 1's than 0's. The circular autocorrelation of a maximal-length sequence or m-sequence with itself has one value of $2^{n-1}$ at zero lag and the rest of the values equal to $2^{n-2}$. Although the non-zero value at the other lag is undesirable, it results in a finite transmission of a DC component through the system which can be removed through filtering. A bipolar sequence comprising 1's and −1's can have better autocorrelation. However, −1's require phase sensitive detection.

Under another embodiment, multiple identical code sequences of 2, 3, 4, 5, 6, 7, 8, 9, 10, 20, 30, 40, 50, 60, 70, 80, 90, 100, 1,000, 10,000, 100,000, 1,000,000 code sequences or any code sequence in between such code sequences or any range of code sequences in between 2 and 1,000,000 code sequences can be used. A detected signal, e.g. a Raman signal, resulting from the entire set of multiple identical code sequences is correlated with an electronic reference signal or source reference signal of the entire set of multiple identical code sequences. The multiple identical code sequences can be periodic or circular. Use of periodic or circular multiple identical code sequences, particularly for Galois class of codes, results in high autocorrelations approaching the delta function and low cross-correlation. This characteristic allows for simultaneous transmission of multiple code sequences and analysis of the multiple code sequences without interference from each code sequence. Each code sequence can be a separate channel and can start at different times. In addition, the autocorrelation of a single code sequence or the correlation of a detected signal resulting from a single code sequence with an electronic reference signal or source reference signal of a single code sequence can result in significant side-lobes. The side-lobes hinder the processing and analysis for the temporal transfer characteristic or the temporal point spread function and can introduce errors. Use of periodic or circular multiple identical code sequences can significantly reduce or eliminate the side-lobes in the autocorrelation or correlation. However, a long individual code element length can result in long processing time particularly for high number of code elements in each sequence and particularly if a large number of multiple code sequences is utilized.

Absorption and scattering properties of the sample can be obtained from the TPSF's, obtained either through code modulation and demodulation as described above or through sequential excitation and analysis, at the excitation frequency and at the collected Raman frequencies. As previously described, this information can allow the Raman spectrum to be corrected for sample turbidity and extract the intrinsic, or quantitative Raman signal of the sample. Thus, complete tissue characterization including absorption coefficient, scattering coefficient, and Raman signal may be obtained in one measurement with perfect registration, removing the question whether light from one modality traveled the same path as light from another modality, among others registration issues in biomedical optics.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for Raman spectroscopy of human tissue comprising:
    illuminating said human tissue with an amplitude-modulated laser emitting light at a first wavelength;
    collecting elastically scattered excitation light scattered by said human tissue and originating from said laser emitting light for purposes of correction for turbidity-induced variations;
    deriving time domain optical data from signals corresponding to time of detection of said collected light;
    determining a scattering coefficient and an absorption coefficient of said human tissue from said time domain optical data;
    measuring a Raman signal from said human tissue at a first Raman wavelength from said scattered light originating from said laser emitting light; and
    correcting said Raman signal for turbidity-induced variations based on said scattering coefficient and said absorption coefficient of said human tissue from said time domain optical data.

2. The method of claim 1 further comprising:
    determining a diffuse reflectance of said human tissue at said first wavelength.

3. The method of claim 1 further comprising:
    deriving a temporal point spread function of said Raman signal of said human tissue at said first Raman wavelength.

4. The method of claim 3 further comprising:
    determining said scattering coefficient of said human tissue at said first Raman wavelength based on said temporal point spread function; and
    determining said absorption coefficient of said human tissue at said first Raman wavelength based on said temporal point spread function.

5. The method of claim 1 further comprising:
    sweeping said laser over a range of wavelengths.

6. The method of claim 1 wherein said first Raman wavelength is a Stokes Raman wavelength.

7. The method of claim 1 wherein said first Raman wavelength is an Anti-Stokes Raman wavelength.

8. A method for Raman spectroscopy of human tissue comprising:
    illuminating said human tissue with an amplitude-modulated laser emitting light at a first wavelength;
    collecting elastically scattered excitation light scattered by said human tissue and originating from said laser emitting light for purposes of correction for turbidity-induced variations;
    deriving time domain optical data from signals corresponding to time of detection of said collected light;
    determining a scattering coefficient of said human tissue based on said time domain optical data;
    determining an absorption coefficient of said human tissue based on said time domain optical data;
    measuring a Raman signal from said human tissue at a first Raman wavelength from said scattered light; and
    correcting said Raman signal for turbidity-induced variations based on said scattering coefficient and said absorption coefficient based on said time domain optical data.

9. The method of claim 8 wherein said first Raman wavelength is a Stokes Raman wavelength.

10. The method of claim 8 wherein said first Raman wavelength is an Anti-Stokes Raman wavelength.

11. The method of claim 8 further comprising:
    sweeping said laser over a range of wavelengths.

12. The method of claim 8 wherein said scattering coefficient of said human tissue is determined at said first wavelength and said absorption coefficient of said human tissue is determined at said first wavelength.

13. A system for Raman spectroscopy comprising:
a frequency sweeping laser light source for illuminating a sample;
a filter positioned after said sample in an optical path from said laser light source to said sample for allowing Raman wavelengths of scattered light from said sample to pass through said filter;
a detector positioned after said filter in said optical path from said laser light to said sample and said filter for detecting an optical signal of said Raman wavelengths of scattered light from said sample corresponding to time of detection of said scattered light; and
a processor configured to correct said optical signal for turbidity-induced variations based on a scattering coefficient and an absorption coefficient of said sample determined with time domain optical data of said scattered light originating from said laser light source.

14. The system of claim 13 wherein said filter is tilted at an angle off-axis with respect to an axis of said light from said sample.

15. The system of claim 13 further comprising:
a signal generator coupled to said laser light source configured to generate a digital modulation signal associated with a pseudo-random code sequence; and
a processor coupled to said detector configured to derive a temporal point spread function of said sample from said light from said sample.

* * * * *